United States Patent
Peters et al.

(10) Patent No.: US 6,645,977 B1
(45) Date of Patent: Nov. 11, 2003

(54) 8-AZABICYCLO(3,2,1)OCT-2-ENE AND OCTANE DERIVATIVES AS CHOLINERGIC LIGANDS AT NICOTINIC ACH RECEPTORS

(75) Inventors: Dan Peters, Arlov (SE); Gunnar M. Olsen, Ballerup (DK); Simon Feldbaek Nielsen, Ballerup (DK); Elsebet Ostergaard Nielsen, Ballerup (DK)

(73) Assignee: NeuroSearch A/S, Ballerup (DK)

( * ) Notice: Subject to any disclaimer, the term of this patent is extended or adjusted under 35 U.S.C. 154(b) by 0 days.

(21) Appl. No.: 09/450,637

(22) Filed: Nov. 29, 1999

Related U.S. Application Data

(63) Continuation of application No. PCT/DK98/00225, filed on May 29, 1998.

(30) Foreign Application Priority Data

| May 30, 1997 | (DK) | ................................................ 0627/97 |
| Dec. 19, 1997 | (DK) | ................................................ 1502/97 |
| Mar. 24, 1998 | (DK) | ................................................ 0408/98 |
| Apr. 16, 1998 | (DK) | ................................................ 0534/98 |

(51) Int. Cl.$^7$ ...................... A61K 31/46; C07D 451/02; A61P 25/30; A61P 25/34

(52) U.S. Cl. ...................... 514/304; 546/132; 546/130; 546/126; 546/125; 546/124

(58) Field of Search ................... 546/130, 126, 546/125, 124, 132; 514/304

(56) References Cited

U.S. PATENT DOCUMENTS

| 3,133,073 A | 5/1964 | Archer ........................ 260/292 |
| 3,657,257 A | * 4/1972 | Helsley ........................ 260/292 |
| 4,590,270 A | 5/1986 | Kompis et al. |
| 4,774,249 A | 9/1988 | Kompis et al. |
| 5,045,546 A | 9/1991 | Hrib et al. |
| 5,731,317 A | * 3/1998 | Lu ............................... 514/289 |
| 6,107,307 A | * 8/2000 | Audia ........................... 514/304 |

FOREIGN PATENT DOCUMENTS

| DE | 2143587 | 3/1972 |
| EP | 0122580 A1 | 10/1984 |
| EP | 0498331 A1 | 8/1992 |
| GB | 2247886 A | 3/1992 |
| GB | 2298647 A | 9/1996 |
| WO | WO9221339 A1 | 12/1992 |
| WO | WO9631508 A1 | 10/1996 |
| WO | WO9711072 A1 | 3/1997 |
| WO | WO9713770 A1 | 4/1997 |
| WO | 98/46600 | * 10/1998 |
| WO | 99/65492 | * 12/1999 |

OTHER PUBLICATIONS

Repke et al., *J. Org. Chem.*, vol. 59, pp. 2164–2171 (1994).
Perregaard et al., *J. Med. Chem.*, vol. 38, pp. 1998–2008 (1995).
Lyle et al., *The Journal of Organic Chemistry*, vol. 35, No. 3, pp. 802–805 (Mar. 1970).
Archer et al., *Nucleophilic Agents on 3$_\alpha$–Chlorotropane*, vol. 80, pp. 4677–4681 (Sep. 5, 1958).
Zirkle et al., *Synthesis of the Tropane–3–Carboxylic Acids*, vol. 27, pp. 1269–1279 (Apr. 1962).
Prokai–Tatrai et al., *Journal of Organometallic Chemistry*, vol. 315, pp. 231–236 (1986).
Banach et al., *Journal of Molecular Catalysis*, vol. 31, pp. 15–37 (1985).
Hanisch et al., *J.C.S. Perkin II*, pp. 1202–1208 (1977).
Freter, *J. Org. Chem.*, vol. 40, No. 17 (1975).
Lyle et al., *Journal of the American Chemical Society*, 89:17, pp. 4563–4564 (XP 000612176) (Aug. 1967).

(List continued on next page.)

Primary Examiner—Evelyn Mei Huang
(74) Attorney, Agent, or Firm—Birch Stewart Kolasch & Birch LLP

(57) ABSTRACT

The present invention discloses compounds of formula (1) any of its enantiomers or any mixture thereof, or a pharmaceutically acceptable salt thereof; wherein - - - - is a single or a double bond; R is hydrogen, alkyl, alkenyl, alkynyl, cycloalkyl,

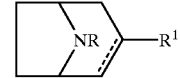

(1)

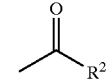

(a)

cycloalkylalkyl, aryl or aralkyl; and R$^1$ is (a), wherein R$^2$ is hydrogen, alkyl, alkenyl, alkynyl, cycloalkyl, cycloalkylalkyl, amino; or aryl which may be substituted one or more times with substituents selected from the group consisting of alkyl, cycloalklyl, cycloalkylalkyl alkenyl, alkynyl, alkoxy, cycloalkoxy, thioalkoxy, thiocycloalkoxy, methylenedioxy, aryloxy, halogen, CF$_3$, OCF$_3$, CN, amino, aminoacyl, nitro, aryl and a monocyclic 5 to 6-membered heteroaryl group; a monocyclic 5 to 6-membered heteroaryl group which may be substituted one or more times with substituents selected from the group consisting of alkyl, cycloalkyl, cycloalkylalkyl alkenyl, alkynyl, alkoxy, cycloalkoxy, thioalkoxy, thiocycloalkoxy, methylenedioxy, aryloxy, halogen, CF$_3$, OCF$_3$, CN, amino, nitro, aryl and a monocyclic 5 to 6-membered heteroaryl group; or a bicyclic heteroaryl group composed of a monocyclic 5 to 6 membered heteroaryl group fused to a benzene ring or fused to another monocyclic 5 to 6-membered heteroaryl, all of which may be substituted one or more times with substituents selected from the group consisting of alkyl, cycloalkyl, cycloalkylalkyl alkenyl, alkynyl, alkoxy, cycloalkoxy, thioalkoxy, thiocycloalkoxy methylenedioxy, aryloxy, halogen, CF$_3$, OCF$_3$, CN, amino, nitro, aryl and a monocyclic 5 to 6-membered heteroaryl group. The compounds of the invention are useful as nicotinic ACh receptor ligands.

6 Claims, No Drawings

OTHER PUBLICATIONS

Beckmann–Umlagerung et al., *Helvetica Chimica Acta*, vol. 51, No. 1, pp. 153–163 (1968).

*The Lancet*, Nicotine and Tourette's Syndrome, p. 1046 (Oct. 28, 1989).

Merriam et al., *Psychiatric Annale*, vol. 23, No. 4, pp. 171–178 (Apr. 1993).

Adler et al., *Biol. Psychiatry*, vol. 32, pp. 607–616 (1992).

Rowell et al., *Journal of Neurochemistry*, vol. 43, No. 6, pp. 1593–1595 (1984).

Hall et al., *Biochemical Pharmacology*, vol. 21, pp. 1829–1838 (1972).

Bourgoin et al., *Naunyn–Schmiedeberg's Arch. Pharmacol.*, vol. 296, pp. 91–97 (1977).

Sershen et al., *Neurochemical Research*, vol. 17, No. 3, pp. 265–271 (1992).

\* cited by examiner

8-AZABICYCLO(3,2,1)OCT-2-ENE AND OCTANE DERIVATIVES AS CHOLINERGIC LIGANDS AT NICOTINIC ACH RECEPTORS

This application is a Continuation of PCT International Application No. PCT/DK98/00225 filed on May 29, 1998, which designated the United States, and on which priority is claimed under 35 U.S.C. §120, the entire contents of which are hereby incorporated by reference.

The present invention relates to novel 8-Azabicyclo [3.2.1]oct-2-ene and -octane derivatives which are cholinergic ligands at nicotinic ACh receptors. The compounds of the invention are useful for the treatment of condition or disorders or diseases involving the cholinergic system of the central nervous system, pain, inflammatory diseases, diseases caused by smooth muscle contractions and as assistance in the cessation of chemical substance abuse.

BACKGROUND

The endogenous cholinergic neurotransmitter, acetyicholine, exert its biological effect via two types of cholinergic receptors; the muscarinic ACh receptors and the nicotinic ACh receptors. As it is well established that muscarinic ACh receptors dominate quantitatively over nicotinic ACh receptors in the brain area important to memory and cognition, much research aimed at the development of agents for the treatment of memory related disorders have focused on the synthesis of muscarinic ACh receptor modulators. Recently, however, an interest in the development of nicotinic ACh receptor modulators has emerged. Several diseases are associated with degeneration of the cholinergic system i.e. senile dementia of the Alzheimer type, vascular dementia and cognitive impairment due to the organic brain damage disease related directly to alcoholism. Indeed several CNS disorders can be attributed to a cholinergic deficiency, a dopaminergic deficiency, an adrenergic deficiency or a serotonergic deficiency. Alzheimer's disease is characterised by a profound loss of memory and cognitive functions caused by a severe depletion of cholinergic neurons, i.e. neurons that release acetyicholine. A reduction in the number of nicotinic ACh receptors are also observed with the progression of Alzheimer's disease. It is believed that the neurons in the cortex that die with the progression of Alzheimer's disease do so because of lack of stimulation of the nicotinic ACh receptors. It is predicted that treatment of Alzheimer's patients with nicotinic ACh receptor modulators will not only improve the memory of patients but in addition act to keep these neurons alive. Smoking actually seems to protect individuals against neurodegeneration and compounds behaving on these receptor may very likely have a generally neuroprotective effect.

However degeneration of the cholinergic system is not limited to individuals suffering from i.e. Alzheimers disease but is also seen in healthy aged adults and rats. Therefore it is suggested that the cholinergic system is involved in and partly responsible for the memory disturbances seen in aged animals and humans. Nicotine receptor modulator may therefore be useful in the treatment of Alzheimer's disease, memory loss, memory dysfunction, AIDS-dementia, senile dementia or neurodegenerative disorders.

Parkinsons disease appears to involve degeneration of dopaminergic neurons. One symptom of the disease has been observed to be loss of nicotinic receptors associated with the dopaminergic neurons and possibly interfering with the process of release of dopamine. As sustained nicotine administration increases the number of receptors present, administration of nicotine receptor modulators may ameliorate the symptoms of Parkinson's disease. Other condition or disorders or disease ascribed to deficiencies in the dopaminergic system is: drug addiction, depression, obesity and narcolepsy.

Tourette's syndrome is a neuropsychiatric disorder involving a range of neurological and behavioral symptoms. It is believed that neurotransmitter dysfunction is involved though the pathophysiology is still unknown and that nicotine will be beneficial in the treatment of the disease (Devor et. al. The Lancet, vol. 8670 p. 1046, 1989)

Schizophrenia is a severe psychiatric illness. Neuroleptic compounds has been used in the treatment of the disease, the effect of the compounds is believed to be interaction in the dopaminergic system. Nicotine is proposed to be effective in the treatment of schizophrenia (Merriam et. al. Psychiatr. annals, Vol. 23, p. 171–178,1993 and Adler et. al. Biol. Psychiatry, Vol. 32, p. 607–616, 1992.)

Nicotine has been reported to have en effect on neurotransmitter release in several systems. Release of acetylcholine and dopamine by neurons upon administration of nicotine has been reported (J. Neurochem. vol. 43, 1593–1598, 1984) and release of norepinephrine by Hall et. al. (Biochem. Pharmacol. vol. 21, 1829–1838, 1972) Release of serotonin by Hery et. al. (Arch. Int. Pharmacodyn. Ther. vol. 296. p. 91–97, 1977). Release of glutamate by Toth et. al (Neurochem. Res. vol. 17, p. 265–271, 1992).

The serotonin system and dysfunction's of the serotonergic system is believed to be involved in diseases or conditions or disorders like: anxiety, depression, eating disorders, obsessive compulsive disorder, panic disorders, chemical substance abuse, alcoholism, pain, memory deficits and anxiety, pseudodementia, Ganser's syndrome, migraine pain, bulimia, obesity, pre-menstrual syndrome or late luteal phase syndrome, tobacco abuse, post-traumatic syndrome, social phobia, chronic fatigue syndrome, premature ejaculation, erectile difficulty, anorexia nervosa, disorders of sleep, autism, mutism or trichotillomania.

Nicotine improves concentration and task performance. Therefore compounds exhibiting nicotine receptor modulating properties will be likely to be useful compounds in the treatment of learning deficit, cognition deficit, attention deficit, attention deficit hyperactivity disorder and dyslexia.

Tobacco use and especially cigarette smoking is recognised as a serious health problem. However nicotine withdrawal symptoms associated with smoking cessation makes it difficult to break this habit. Withdrawal symptoms include anger, anxiety, difficulties in concentrating, restlessness, decreased heart rate and increased appetite and weight gain. Nicotine itself has shown to ease the withdrawal symptoms.

Withdrawal from addictive substances, i.e. opiates, benzodiazepines, ethanol, tobacco or nicotine, is in general a traumatic experience characterised by anxiety and frustration. Nicotine has been found to be effective in reducing anger, irritability, frustration and feelings of tension without causing general response depression, drowsiness or sedation and compounds having same characteristics as nicotine is likely to have same effects.

Mild to moderate pain is normally treatable with NSAID's (non-steroidal anti-inflammatory drugs) while opiates are used preferentially for moderate to severe pain. The opiates have some well-known side-effects, including chemical dependence and abuse potential as well as a depressive effect on the respiratory and gastrointestinal system. There exists therefore a strong need for analgesic compounds that do not exhibit these side effects and which can relieve mild, moderate and severe pain of acute, chronic or recurrent character as well as migraine pain and postoperative pain, phantom limb pain.

Epibatidine, a compound isolated from the skin of a poison frog, is a very potent analgesic with an approximate potency of 500 times that of morphine. The analgesic effect is not affected by naloxone, which is an indication of a negligible affinity for the opiate receptors. Epibatidine is an nicotinic cholinergic receptor agonist and it is therefore very likely, that compounds possessing this receptor modulating character will also show a strong analgesic response. The compounds of the present invention has proven useful for modulation of smooth muscle contractions and may therefore be used in the treatment or prevention of condition or disorders or diseases inherent from smooth muscle contractions like i.e. convulsive disorders, angina pectoris, premature labor, convulsions, diarrhoea, asthma, epilepsy, tardive dyskinesia, hyperkinesia.

Further, it is well known that nicotine has an effect on appetite and it is predicted that modulators at the nicotine ACh receptor may be useful as appetite suppressants in the treatment of obesity and eating disorders.

The cholinergic receptors play an important role in the functioning of muscles, organs and generally in the central nervous system. There are also complex interactions between cholinergic receptors and the function of receptors of other neurotransmitters such as dopamine, serotonin and noradrenaline.

It is likely that nicotine receptor modulator compounds can be effective in preventing or treating conditions or disorders or diseases like: inflammation, inflammatory skin conditions, Chron's disease, inflammatory bowel disease, ulcerative collitis, diarrhoea, neurodegeneration, perpherical neuropathy, amyotrophic lateral sclerosis, nociception, endocrine disorders, thyrotoxicosis, pheochromocytoma, hypertension, arrhytmias, mania, manic depression, Huntington's disease, jetlag.

The compounds of the present invention are nicotine receptor modulators and has the potential to exhibit nicotinic pharmacology, preferentially without the side effects associated with nicotine itself. Additionally, the compounds are expected to have the potential as enhancers of neurotransmitter secretion and suppress symptoms associated with a low activity of neurotransmitters.

Structural close analogues to the compounds of the present invention are described in EP 122580 which describes pyrimidine derivatives as dihydrofolate reductase inhibitors useful against bacterial infections and malaria.

GB 2298647 describes bridged piperidines which promotes the release of growth hormone.

WO 97/13770 describes monoamine neurotransmitter reuptake inhibitors.

EP 0498331 which describes N-(aryloxyalkyl)-heteroaryl-8-azabicyclo(3.2.1)octanes as antipsychotic agents and as inhibitors of the reuptake of serotonin.

J. Med. Chem. 1995, 38, 1998–2008, describes σ-ligands with potential anxiolytic activity.

J. Org. Chem. 1994, 59, 2164–2171, describes abbreviated Ibogaine congeners.

There is thus a large need for the development of nicotinic ACh receptor modulators with a more favourable pharmacological profile. A favourable pharmacological profile meaning for example:

A high binding selectivity for the receptor subtypes of neuronal nAChR's, e.g. the α7-subtype A low affinity for the muscular subtype.
An induction of cell survival.
An oral efficacy in vivo (rat model) of arousal/attention.
A low toxicity in vivo.
A non-mutagenic compound According to the present invention valuable modulators of the nicotinic cholinergic receptors are provided. Certain compounds which are antagonists at the nicotinic ACh receptor may be useful for the treatment of transient anoxia and induced neurodegeneration.

OBJECTS OF THE INVENTION

It is an object of the present invention to provide novel 8-Azabicyclo[3.2.1]oct-2-ene and -octane derivatives which are useful for the treatment of a range of diseases or conditions or disorders characterised by decreased cholinergic function or responsive to the activity of nicotinic ACh receptor modulators.

Another object of the present invention is to provide novel pharmaceutical compositions containing these compounds, as well as methods for the preparation thereof and methods for the treatment therewith.

It is yet another object of the invention to provide novel compounds that have some if not all of the following favourable characteristics:

A high binding selectivity for the receptor subtypes of neuronal nAChR's, e.g. the α7 subtype.
A low affinity for the muscular subtype.
An induction of cell survival.
An oral efficacy in vivo of arousal/attention.
A low toxicity in vivo.
A non-mutagenic compound.
Other objects will become apparent hereinafter to one skilled in the art.

THE PRESENT INVENTION

In the context of this invention "treating" covers treatment, prevention, profylaxis or alleviation and "disease" covers a disease or a disorder or a condition; In the context of this invention "modulator" covers agonists, partial agonists, antagonists and allosterical modulators.

In the context of this invention disorders in the central nervous system covers for example: neurodegenerative disorders, cognitive or memory dysfunction, Alzheimer's disease, Parkinson's disease, Huntington's disease, Amyotrophic Lateral Sclerosis, Gilles de la Tourettes syndrome, attention deficit hyperactivity disorder, anxiety, depression, mania, manic depression, schizophrenia, obsessive compulsive disorders, eating disorders like anorexia nervosa, bulimia and obesity, narcolepsy, nociception, memory loss, memory dysfunction, AIDS-dementia, senile dementia, peripherial neuropathy, learning deficit, cognition deficit, attention deficit, autism, dyslexia, tardive dyskinesia, hyperkinesia, epilepsy, bulimia, post-traumatic syndrome, social phobia, chronic fatigue syndrome, disorders of sleep, pseudodementia, Ganser's syndrome, prementraul syndrome, late luteal phase syndrome, chronic fatigue syndrome, premature ejaculation, erectile difficulty, mutism and trichotillomania.

In the context of this invention inflammatory conditions covers for example: inflammatory skin conditions like acne and rosacea, Chron's disease, inflammatory bowel disease, ulcerative collitis, diarrhoea.

Diseases associated with smooth muscle contractions covers for example: convulsive disorders, angina pectoris, premature labor, convulsions, diarrhoea, asthma, epilepsy, tardive dyskinesia, hyperkinesia.

In the context of this invention pain covers for example chronic, acute and recurrent pain, postoperative pain, migraine pain or phantom limb pain;

Abuse of chemical substances covers smoking as well as use of other nicotine containing products, use of opiods like heroin, cocaine and morphine, use of benzodiazepines or alcohol. In this context "treatment" covers treatment, prevention, profylaxis and alleviation of withdrawal symptoms and abstinence as well as treatment resulting in a voluntary diminished intake of the addictive substance.

The invention then, inter alia, comprises the following, alone or in combination:

A compound having the formula,

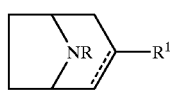

1 any of its enantiomers or any mixture thereof, or a pharmaceutically acceptable salt thereof;
wherein
- - - - is a single or a double bond;
R is hydrogen, alkyl, alkenyl, alkynyl, cycloalkyl, cycloalkylalkyl, aryl or aralkyl; and

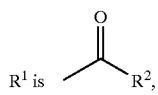

wherein $R^2$ is hydrogen, alkyl, alkenyl, alkynyl, cycloalkyl, cycloalkylalkyl, amino; or
aryl which may be substituted one or more times with substituents selected from the group consisting of alkyl, cycloalkyl, cycloalkylalkyl alkenyl, alkynyl, alkoxy, cycloalkoxy, thioalkoxy, thiocycloalkoxy, methylenedioxy, aryloxy, halogen, $CF_3$, $OCF_3$, CN, amino, aminoacyl, nitro, aryl and a monocyclic 5 to 6 membered heteroaryl group;
a monocyclic 5 to 6 membered heteroaryl group which may be substituted one or more times with substituents selected from the group consisting of alkyl, cycloalkyl, cycloalkylalkyl alkenyl, alkynyl, alkoxy, cycloalkoxy, thioalkoxy, thiocycloalkoxy, methylenedioxy, aryloxy, halogen, $CF_3$, $OCF_3$, CN, amino, nitro, aryl and a monocyclic 5 to 6 membered heteroaryl group; or
a bicyclic heteroaryl group composed of a monocyclic 5 to 6 membered heteroaryl group fused to a benzene ring or fused to another monocyclic 5 to 6 membered heteroaryl, and which may be substituted one or more times with substituents selected from the group consisting of alkyl, cycloalkyl, cycloalkylalkyl alkenyl, alkynyl, alkoxy, cycloalkoxy, thioalkoxy, thiocycloalkoxy, methylenedioxy, aryloxy, halogen, $CF_3$, $OCF_3$, CN, amino, nitro, aryl and a monocyclic 5 to 6 membered heteroaryl group;

A preferred embodiment of the invention is a compound of formula 1 wherein
R is hydrogen, alkyl, alkenyl, alkynyl, cycloalkyl, cycloalkylalkyl, aryl or aralkyl; and

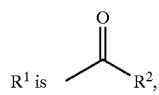

wherein $R^2$ is hydrogen, alkyl, alkenyl, alkynyl, cycloalkyl, cycloalkylalkyl, amino; or
aryl which is substituted one or more times with substituents selected from the group consisting of cycloalkyl, cycloalkylalkyl alkenyl, alkynyl, alkoxy, cycloalkoxy, thioalkoxy, thiocycloalkoxy, methylenedioxy, aryloxy, $OCF_3$, CN, amino, aminoacyl, nitro, aryl and a monocyclic 5 to 6 membered heteroaryl group;
a monocyclic 5 to 6 membered heteroaryl group which may be substituted one or more times with substituents selected from the group consisting of alkyl, cycloalkyl, cycloalkylalkyl alkenyl, alkynyl, alkoxy, cycloalkoxy, thioalkoxy, thiocycloalkoxy, methylenedioxy, aryloxy, halogen, $CF_3$, $OCF_3$, CN, nitro, aryl and a monocyclic 5 to 6 membered heteroaryl group; or
a bicyclic heteroaryl group composed of a monocyclic 5 to 6 membered heteroaryl group with one heteroatom, fused to a benzene ring or fused to another monocyclic 5 to 6 membered heteroaryl, all of which may be substituted one or more times with substituents selected from the group consisting of alkyl, cycloalkyl, cycloalkylalkyl alkenyl, alkynyl, alkoxy, cycloalkoxy, thioalkoxy, thiocycloalkoxy, methylenedioxy, aryloxy, halogen, $CF_3$, $OCF_3$, CN, amino, nitro, aryl and a monocyclic 5 to 6 membered heteroaryl group;

Another preferred embodiment of the invention is compound of formula 1 wherein
R is hydrogen, methyl, ethyl or benzyl;
$R^1$ is acetyl, 2-methoxyphenyl, 2-naphtyl, 3-acetamidophenyl, 2-selenophenyl 3-pyridyl, 3-(6-methoxy)pyridyl, 3-(6-chloro)pyridyl, 2-thiazolyl, 3-thienyl, 2-thienyl, 2-methoxymethyl)thienyl, 2-furyl, 3-furyl, 2-(3-bromo)thienyl), 3-chloro-thien-2-yl, 3-(3-furyl)2-thienyl, 3-quinolinyl, 3-benzofuryl, 2-benzofuryl, 3-benzothienyl, 2-benzothienyl, 2-benzothiazolyl, 2-thieno[3.2-b]thienyl, thieno[2.3-b]thienyl, 2-(3-bromo)benzofuryl or 2-(3-bromo)benzothienyl;

A further embodiment of the invention is a compound as above which is
(±)-8-Benzyl-3-(3-pyridyl)-8-azabicyclo[3.2.1]oct-2-ene;
(±)-8-Methyl-3-(3-pyridyl)-8-azabicyclo[3.2.1]oct-2-ene;
(±)-8-Methyl-3-(3-quinolinyl)-8-azabicyclo[3.2.1]oct-2-ene;
(±)-3-(3-Benzofuryl)-8-methyl-8-azabicyclo[3.2.1]oct-2-ene;
(±)-3-(3-Benzothienyl)-8-methyl-8-azabicyclo[3.2.1]oct-2-ene;
(±)-3-(2-Thiazolyl)-8-Methyl-8-azabicyclo[3.2.1]oct-2-ene;
(±)-8-Methyl-3-(2-methoxyphenyl)-8-azabicyclo[3.2.1]oct-2-ene;
(±)-8-Methyl-3-(3-thienyl)-8-azabicyclo[3.2.1]oct-2-ene;
(±)-8-Methyl-3-(2-naphtyl)-8-azabicyclo[3.2.1]oct-2-ene;
Exo-8-Methyl-3-(3-pyridyl)-8-azabicyclo[3.2.1]octane;

(±)-8-H-3-(3-Pyridyl)-B-azabicyclo[3.2.1]oct-2-ene;
(±)-8-Methyl-3-[3-(6-methoxy)-pyridyl]-8-azabicyclo [3.2.1]oct-2-ene;
(±)-3-Acetyl-8-methyl-8-azabicyclo[3.2.1]oct-2-ene;
(±)-8-Methyl-3-[3-(6-chloro)-pyridyl]-8-azabicyclo [3.2.1]oct-2-ene;
(±)-3-(2-Benzofuryl)-8-methyl-8-azabicyclo[3.2.1]oct-2-ene;
(±)-3-(2-Benzothienyl)-8-methyl-8-azabicyclo[3.2.1]oct-2-ene;
(±)-3-(3-Acetamidophenyl)-8-methyl-8-azabicyclo [3.2.1]oct-2-ene;
(±)-3-(3-Aminophenyl) 8-methyl-8-azabicyclo[3.2.1]oct-2-ene;
(±)-3-(2-Thienyl)-8-methyl-8-azabicyclo[3.2.1]oct-2-ene;
(±)-3-[2-(3-Methoxymethylthienyl)]-8-methyl-8-azabicyclo[3.2.1]oct-2-ene;
(±)-3-(2-Benzothiazolyl)-8-methyl-8-azabicyclo[3.2.1] oct-2-ene;
(±)-3-(2-Furyl)-8-methyl-8-azabicyclo[3.2.1]oct-2-ene;
(±)-3-(2-Thieno[3.2-b]thienyl)-8-methyl-8azabicyclo [3.2.1]oct-2-ene;
(±)-3-(2-Thieno[2.3-b]thienyl)-8-methyl-8-azabicyclo [3.2.1]oct-2-ene;
(±)-3-(2-Selenophenyl)-8-methyl-8-azabicyclo[3.2.1]oct-2-ene;
(±)-3-(2-Benzofuryl)-8-H-8-azabicyclo[3.2.1]oct-2-ene;
(±)-3-[3-(3-Furyl)-2-thienyl]-8-H-8-azabicyclo[3.2.1] oct-2-ene;
(±)-3-(2-Benzofuryl)-8-ethyl-8-azabicyclo[3.2.1]oct-2-ene;
(±)-3-[2-(3-Bromothienyl)]-8-methyl-8-azabicyclo[3.2.1] oct-2-ene;
(±)-3-[2-(3-Bromobenzofuryl)]-8-methyl-8-azabicyclo [3.2.1)oct-2-ene;
(±)-3-[2-(3-Bromobenzothienyl)]-8-methyl-8-azabicyclo [3.2.1)oct-2-ene;
3-[2-(3-Chlorothienyl)]-8-methyl-8-azabicyclol3.2.1]oct-2-ene or
(±)-3-[3-(3-Furyl)-2-thienyl]-8-methyl-8-azabicyclo [3.2.1]oct-2-ene;
or a pharmaceutically acceptable addition salt thereof;
a pharmaceutical composition, comprising a therapeutically effective amount of a compound as above, or a pharmaceutically acceptable addition salt thereof, together with at least one pharmaceutically acceptable carrier or diluent;
the use of a compound as above for the manufacture of a medicament for the treatment or prevention of a condition or disorder or disease of a living animal body, including a human, which condition or disorder or disease is responsive to the activity of nicotinic ACh receptor modulators;
the use of a compound as above wherein the disease to be treated is pain, a disease in the central nervous system, a disease caused by smooth muscle contraction, neurodegeneration, inflammation, chemical substance abuse or withdrawal symptoms caused by the cessation of intake of the chemical substance.
The use as above wherein the disease is a disease in the central nervous system said disease being Alzheimer's disease, Parkinson's disease, memory dysfunction or attention deficit hyperactivity disorder.
The use as above wherein the disease to be treated is chemical substance abuse or withdrawal symptoms caused by the cessation of intake of the chemical substance, said chemical substance abuse being smoking or use of other nicotine containing products and withdrawal symptoms caused by cessation of use of nicotine containing products;
   a method for the preparation of the compounds as above comprising the step of reacting a compound having the formula
   a) the step of reacting a compound having the formula

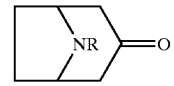

wherein R is as defined above, with a compound of the formula $R^1$—Li, wherein $R^1$ is as defined above followed by dehydration of the compound obtained;
   b) the step of reacting a compound having the formula

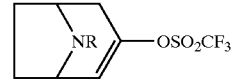

wherein R is as defined above, with a compound of formula $R^1$—X, wherein $R^1$ is as defined above and X is halogen, boronic acid, or trialkylstannyl; or
   c) the step of reducing a compound having the formula

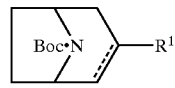

wherein $R^1$ is as defined above;
   a method of treating a disease of a living animal body, including a human, which disease is responsive to the activity of nicotinic ACh receptor modulators, comprising the step of administering to such a living animal body, including a human, in need thereof a therapeutically effective amount of a compound as above;
   the method as above wherein pain, a disease of the central nervous system, neurodegeneration, inflammation, chemical substance abuse, withdrawal symptoms from cessation of use of addictive substances, or a disease caused by smooth muscle contractions is treated;
The method as above wherein chemical substance abuse or withdrawal symptoms caused by the cessation of intake of the chemical substance, said chemical substance abuse being smoking or use of other nicotine containing products and withdrawal symptoms caused by cessation of use of nicotine containing products, is treated;
The method as above wherein a disease in the central nervous system, said disease being Alzheimer's disease, Parkinson's disease, memory dysfunction or attention deficit hyperactivity disorder, is treated;
Examples of pharmaceutically acceptable addition salts include inorganic and organic acid addition salts such as the hydrochloride, hydrobromide, phosphate, nitrate, perchlorate, sulphate, citrate, lactate, tartrate, maleate, fumarate, mandelate, benzoate, ascorbate, cinnamate, benzenesulfonate, methanesulfonate, stearate, succinate, glutamate, glycollate, toluene-p-sulphonate, formate, malonate, naphthalene-2-sulphonate, salicylate and the acetate. Such salts are formed by procedures well known in the art.

Other acids such as oxalic acid, while not in themselves pharmaceutically acceptable, may be useful in the preparation of salts useful as intermediates in obtaining compounds of the invention and their pharmaceutically acceptable acid addition salts.

Halogen is fluorine, chlorine, bromine or iodine.

Alkyl means a straight chain or branched chain of one to six carbon atoms, including but not limited to, methyl, ethyl, propyl, isopropyl, butyl, isobutyl, t-butyl, pentyl, and hexyl; methyl, ethyl, propyl and isopropyl are preferred groups.

Cycloalkyl means cyclic alkyl of three to seven carbon atoms, including but not limited to cyclopropyl, cyclobutyl, cyclopentyl, and cyclohexyl;

Alkenyl means a group of from two to six carbon atoms, including at least one double bond, for example, but not limited to ethenyl, 1,2- or 2,3-propenyl, 1,2-, 2,3-, or 3,4-butenyl.

Alkynyl means a group of from two to six carbon atoms, including at least one triple bond, for example, but not limited to ethynyl, 1,2- or 2,3-propynyl, 1,2- or 2,3- or 3,4-butynyl.

Cycloalkylalkyl means cycloalkyl as above and alkyl as above, meaning for example, cyclopropylmethyl.

Alkoxy is O-alkyl, wherein alkyl is as defined above.

Cycloalkoxy is O-cycloalkyl, wherein cycloalkyl is as defined above.

Thioalkoxy is S-alkyl, wherein alkyl is as defined above.

Thiocycloalkoxy is S-cycloalkyl, wherein cycloalkyl is as defined above.

Amino is $NH_2$ or NH-alkyl or N—alkyl)$_2$, wherein alkyl is as defined above.

Acyl is (C=O)—R° or (C=S)—R° wherein R° is alkyl, alkoxy, aryl or aryloxy; wherein alkyl and alkoxy is defined above and aryl and aryloxy is defined below;

Aminoacyl is —NH-acyl, wherein acyl is defined above;

A monocyclic 5- to 6-membered heteroaryl group containing one, two, three or four heteroatomes and includes, for example, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-5-yl, 1,2,4-thiadiazol-5-yl, 1,2,5-oxadiazol-3-yl, 1,2,5-oxadiazol4-yl, 1,2,5-thiadiazol-3-yl, 1,2,5-thiadiazol-4-yl, 1-imidazolyl, 2-imidazolyl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl and 3-pyrazinyl and 1-pyrazolyl, 3-pyrazolyl, and 4-pyrazolyl, tetrazolyl.

A bicyclic heteroaryl group composed of a 5 to 6 membered monocyclic heteroaryl group and a fused benzene ring or another 5 to 6 membered monocyclic heteroaryl group, means a monocyclic 5 to 6 membered heteroaryl group as above which is fused to a benzene ring or fused to a 5 to 6 membered heteroaryl as above, including, for example, 2-, 3-, 4-, 5-, 6-, 7-benzofuranyl, 1-, 2-, 4-, 5-benzimidazolyl, 2-, 3-, 4-, 5-, 6-, 7-indolyl, 2-,3-,4-, 5-,6-,7-,8-quinolinyl and 1-,3-,4-,5-,6-,7-,8-isoquinolinyl, thieno[3,2-b]thienyl, thieno[2,3-b] thienyl;

Aryl is an aromatic hydrocarbon, such as phenyl and naphthyl.

Aryloxy is —O-aryl where aryl is defined above.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

It will be appreciated by those skilled in the art that the compounds of the present invention contain several chiral centres and that such compounds exist in the form of isomers (i.e. enantiomers). The invention includes all such isomers and any mixtures thereof including racemic mixtures.

Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can thus be resolved into their optical antipodes, e.g., by fractional crystallization of d- or l- (tartrates, mandelates, or camphorsulphonate) salts for example. The compounds of the present invention may also be resolved by the formation of diastereomeric amides by reaction of the compounds of the present invention with an optically active activated carboxylic acid such as that derived from (+) or (−)phenylalanine, (+) or (−)phenylglycine, (+) or (−)camphanic acid or by the fornation of diastereomeric carbamates by reaction of the compounds of the present invention with an optically active chloroformate or the like.

Additional methods for the resolvation of optical isomers, known to those skilled in the art may be used, and will be apparent to the average worker skilled in the art. Such methods include those discussed by J. Jaques, A. Collet, and S. Wilen in "Enantiomers, Racemates, and Resolutions", John Wiley and Sons, New York (1981).

Optical active compounds can also be prepared from optical active starting materials.

The compounds of the invention may be prepared by any conventional method useful for the preparation of analogous compounds and as described in the examples below.

Starting materials for the processes described in the present patent application are known or can be prepared by known processes from commercially available materials A compound of the invention can be converted to another compound of the invention using conventional methods.

The products of the reactions described herein are isolated by conventional means such as extraction, crystallisation, distillation, chromatography, and the like.

BIOLOGY

Nicotinic ACh receptors in the brain are pentameric structures composed of subunits distinct from those found in skeletal muscles. The existence of eight α-subunits (α2–α9) and three β-subunits (β2–β4) in the mammalian brain has been described.

The predominant subtype with high affinity for nicotine is comprised of three $α_4$ and two $β_2$ subunits.

The affinity of compounds of the invention for nicotinic ACh receptors have been investigated in three test for in vitro inhibition of $^3$H-epibatidin binding, $^3$H-α-bungarotoxin binding and $^3$H-cytisine binding as described below:

In vitro inhibition of $^3$H-cytisine binding

The predominant subtype with high affinity for nicotine is comprised of $α_4$ and $β_2$ subunits. nAChRs of the latter type can selectively be labelled by the nicotine modulator $^3$H-cytisine.

Tissue Preparation: Preparations are performed at 0–4° C. unless otherwise indicated. Cerebral corticies from male Wistar rats (150–250 g) are homogenised for 20 sec in 15 ml Tris, HCl (50 mM, pH 7.4)containing 120 mM NaCl, 5 mM KCl, 1 mM MgCl$_2$ and 2.5 mM CaCl$_2$ using an Ultra-Turrax homogeniser. The homogenate is centrifuged at 27,000×g for 10 min. The supernatant is discarded and the pellet is resuspended in fresh buffer and centrifuged a second time. The final pellet is resuspended in fresh buffer (35 ml per g of original tissue) and used for binding assays.

Assay: Aliquots of 500 μl homogenate are added to 25 μl of test solution and 25 μl of $^3$H-cytisine (1 nM, final concentration), mixed and incubated for 90 min at 2° C. Non-specific binding is determined using (−)-nicotine (100 μM, final concentration). After incubation the samples are added 5 ml of ice-cold buffer and poured directly onto Whatman GF/C glass fibre filters under suction and immediately washed with 2×5 ml ice-cold buffer. The amount of radioactivity on the filters is determined by conventional liquid scintillation counting. Specific binding is total binding minus non-specific binding.

In vitro Inhibition of $^3$H-α-Bungarotoxin Binding Rat Brain

α-Bungarotoxin is a peptide isolated from the venom of the Elapidae snake *Bungarus multicinctus* (Mebs et al., Biochem. Biophys. Res. Commun., 44(3), 711 (1971)) and has high affinity for neuronal and neuromuscular nicotinic receptors, where it acts as a potent antagonist. $^3$H-α-Bungarotoxin binds to a single site in rat brain with an unique distribution pattern in rat brain (Clarke et al., J. Neurosci. 5, 1307–1315 (1985)).

$^3$H-α-Bungarotoxin labels nAChR formed by the ca subunit isoform found in brain and the α$_1$ isoform in the neuromuscular junction (Changeaux, Fidia Res. Found. Neurosci. Found. Lect. 4, 21–168 (1990). Functionally, the α$_7$ homo-oligomer expressed in oocytes has a calcium permeability greater than neuromuscular receptors and, in some instances greater than NMDA channels (Seguela et al., J. Neurosci. 13, 596–604 (1993).

Tissue preparation: Preparations are performed at 0–4° C. unless otherwise indicated. Cerebral cortices from male Wistar rats (150–250 g) are homogenised for 10 sec in 15 ml 20 mM Hepes buffer containing 118 mM NaCl, 4.8 mM KCl, 1.2 mM MgSO$_4$ and 2.5 mM CaCl$_2$ (pH 7.5) using an Ultra-Turrax homogeniser. The tissue suspension is centrifuged at 27,000×g for 10 min. The supernatant is discarded and the pellet is washed twice by centrifugation at 27,000×g for 10 min in 20 ml fresh buffer, and the final pellet is resuspended in fresh buffer containing 0.01% BSA (35 ml per g of original tissue) and used for binding assays.

Assay: Aliquots of 500 μl homogenate are added to 25 μl of test solution and 25 μl of $^3$H-α-bungarotoxin (2 nM, final concentration), mixed and incubated for 2 h at 37° C. Non-specific binding is determined using (−)-nicotine (1 mM, final concentration). After incubation the samples are added 5 ml of ice-cold Hepes buffer containing 0.05% PEI and poured directly onto Whatman GF/C glass fibre filters (presoaked in 0.1% PEI for at least 6 h) under suction and immediately washed with 2×5 ml ice-cold buffer. The amount of radioactivity on the filters is determined by conventional liquid scintillation counting. Specific binding is total binding minus non-specific binding.

In vitro Inhibition of $^3$H-Epibatidin Binding

Epibatidin is an alkaloid that was first isolated from the skin of the Ecuadoran frog *Epipedobates tricolor* and was found to have very high affinity for neuronal nicotinic receptors, where it acts as a potent agonist. 3H-epibatidin binds to two sites in rat brain, both of which have pharmacological profiles consistent with neuronal nicotinic receptors and a similar brain regional distribution (Hougling et al., Mol. Pharmacol. 48, 280–287 (1995)).

The high affinity binding site for $^3$H-epibatidin is most certainly binding to the α$_4$β$_2$ subtype of nicotinic receptors. The identity of the low affinity site is still unknown; does it represent a second nicotinic receptor or a second site in the same receptor. The inability of α-bungarotoxin to compete for $^3$H-epibatidin binding sites indicates that neither site measured represents the nicotinic receptor composed of α$_7$ subunits.

Tissue preparation: Preparations are performed at 0–4° C. unless otherwise indicated. The forebrain (÷cerebellum) from a male Wistar rat (150–250 g) is homogenised for 10–20 sec in 20 ml Tris, HCl (50 mM, pH 7.4) using an Ultra-Turrax homogeniser. The tissue suspension is centrifuged at 27,000×g for 10 min. The supernatant is discarded and the pellet is washed three times by centrifugation at 27,000×g for 10 min in 20 ml fresh buffer, and the final pellet is resuspended in fresh buffer (400 ml per g of original tissue) and used for binding assays.

Assay: Aliquots of 2.0 ml homogenate are added to 0.100 ml of test solution and 0.100 ml of $^3$H-epibatidin (0.3 nM, final concentration), mixed and incubated for 60 min at room temperature. Non-specific binding is determined using (−)-nicotine (30 μM, final concentration). After incubation the samples are poured directly onto Whatman GF/C glass fibre filters (presoaked in 0.1% PEI for at least 20 min) under suction and immediately washed with 2×5 ml ice-cold buffer. The amount of radioactivity on the filters is determined by conventional liquid scintillation counting. Specific binding is total binding minus non-specific binding.

Results are given as IC$_{50}$ values; the concentration (μM) that inhibit binding of the radioactive ligand by 50%.

Below test results for one compound of the invention are presented:
(The Compound Numbers Refers to the Examples.)

| Compound | $^3$H-cytisine IC$_{50}$ (μM) | $^3$H-epibatidin IC$_{50}$ (μM) | $^3$H-α-bungarotoxin IC$_{50}$ (μM) |
|---|---|---|---|
| 1a | 0.023 | 0.0840 | 0.500 |
| 2a | 0.0220 | 0.0800 | 0.550 |
| 3a | 1.300 | 8.000 | 1.440 |
| 4a | 2.700 | 6.300 | 3.500 |
| 5b | 0.020 | 0.091 | 1.900 |
| 2c | 63.80 | 367.0 | 0.100 |
| 3c | 17.0 | >10.0 | 0.640 |
| 4c | 0.030 | 0.200 | 0.440 |
| 1d | 120.000 | 450.000 | 0.170 |
| 2d | 110.000 | 310.000 | 0.0670 |
| 1e | >10.0 | >10.0 | 0.800 |
| 3e | >10.0 | >10.0 | 0.5100 |
| 1f | 2.200 | 2.800 | 0.082 |
| 2f | 30.0 | >10.0 | 1.300 |

PHARMACEUTICAL COMPOSITIONS

In another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers and/or diluents.

In a preferred embodiment, the invention provides pharmaceutical compositions comprising the chemical compound of the invention, or a pharmaceutically acceptable salt or derivative thereof, together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical compositions of the invention may be those suitable for oral, rectal, nasal, topical (including buccal and sub-lingual), transdermal, vaginal or parenteral (including intramuscular, sub-cutaneous and intravenous) administration, or those in a form suitable for administration by inhalation or insufflation.

The chemical compound of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

For topical administration to the epidermis the chemical compound according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size forexample of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

The dose administered must of course be carefully adjusted to the age, weight and condition of the individual being treated, as well as the route of administration, dosage form and regimen, and the result desired. It is presently contemplated that compositions containing of from about 0.1 to about 500 mg of active ingredient per unit dosage, preferably of from about 1 to about 100 mg, most preferred of from about 1 to about 10 mg, are suitable for therapeutic treatments.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

METHOD OF TREATING

The compounds of the present invention are valuable nicotinic ACh receptor modulators and therefore useful for the treatment of a range of ailments involving cholinergic dysfunction as well as a range of disorders responsive to the activity of nicotinic ACh receptor modulators. The compounds may be used in the treatment, prevention, profylaxis or alleviation of a disease, disorder or condition of the central nervous system as for example: neurodegenerative disorders, cognitive or memory dysfunction, Alzheimer's disease, Parkinson's disease, Huntington's disease, Amyotrophic Lateral Sclerosis, Gilles de la Tourettes syndrome, attention deficit hyperactivity disorder, anxiety, depression, mania, manic depression, schizophrenia, obsessive compulsive disorders, eating disorders like anorexia nervosa, bulimia and obesity, narcolepsy, nociception, memory loss, memory dysfunction, AIDS-dementia, senile dementia, peripherial neuropathy, learning deficit, cognition deficit, attention deficit, autism, dyslexia, tardive dyskinesia, hyperkinesia, epilepsy, bulimia, post-traumatic syndrome, social phobia, chronic fatigue syndrome, disorders of sleep, pseudodementia, Ganser's syndrome, prementraul syndrome, late luteal phase syndrome, chronic fatigue syndrome, premature ejaculation, erectile difficulty, mutism and trichotillomania.

The compounds of this invention may also be used in the treatment of inflammatory conditions as for example: inflammatory skin conditions like acne and rosacea, Chron's disease, inflammatory bowel disease, ulcerative collitis, diarrhoea.

Also the compounds of the invention may be used in the treatment of diseases associated with smooth muscle contractions as for example: convulsive disorders, angina pectoris, premature labor, convulsions, diarrhoea, asthma, epilepsy, tardive dyskinesia, hyperkinesia.

The compounds of this invention may also be used in the treatment of pain as for example chronic, acute and recurrent pain, postoperative pain, migraine pain or phantom limb pain;

The compounds of the present invention may also be used for the assistance in cessation of abuse of chemical substances as for example smoking cessation as well as cessation of use of other nicotine containing products, cessation of use of opiods like heroin, cocaine and morphine and cessation of use of benzodiazepines or alcohol. In the context of the present invention "treatment" means as well treatment as prevention, profylaxis and alleviation of withdrawal symptoms and abstinence as well as treatment resulting in a voluntary diminished intake of the addictive substance.

Suitable dosage range are 0.1–500 milligrams daily, and especially 10–70 milligrams daily, administered once or twice a day, dependent as usual upon the exact mode of administration, form in which administered, the indication toward which the administration is directed, the subject involved and the body weight of the subject involved, and further the preference and experience of the physician or veterinarian in charge.

I.p. means intraperetoneally, which is a well known route of administration.

P.o. means peroral, which is a well known route of administration.

The following examples will illustrate the invention further, however, they are not to be construed as limiting.

EXAMPLES

General: All reactions involving air sensitive reagents or intermediates were performed under nitrogen and in anhydrous solvents. Magnesium sulfate was used as drying agent in the workup-procedures and solvents were evaporated under reduced pressure.

Method A

1a: (±)-8-Benzyl-3-(3-pyridyl)-8-azabicyclo[3.2.1] oct-2-ene Fumaric Acid Salt To a mixture of 3-bromopyridine (11.0 g, 69.7 mmol) and diethyl ether (200 ml), butyllithium in hexanes (2.5 M, 30.7 ml, 76.7 mmol) was added at −70° C. The mixture was stirred at −70° C. for 1 h. 8-benzyl-8-azabicyclo[3.2.1] octan-3-one (15.0 g, 69.7 mmol) solved in diethyl ether (80 ml) was added at −70° C. and stirred for 1 h. The reaction mixture was allowed to warm to room temperature overnight. Aqueous sodium hydroxide (1 M, 200 ml) was added and the diethyl ether was separated. The water phase was extracted three times with ethyl acetate (100 ml). The organic phases were mixed. Endo-8-benzyl-3-hydroxy-3-(3-pyridyl)-8-azabicyclo[32.1]octane was isolated after trituration with petroleum ether. Yield 7.0 g, 34%. A mixture of endo-8-benzyl-3-hydroxy-3-(3-pyridyl)-8-azabicyclo[3.2.1] octane (3.0 g, 10.2 mmol), thionyl chloride (9 ml, 123 mmol) and tetrahydrofuran (100 ml) was stirred at 50° C. for 0.5 h. The mixture was evaporated and combined with potassium hydroxide (4.6 g, 82.0 mmol), ethanol (25 ml) and water (25 ml) and stirred for 5 min. The ethanol was evaporated and water (50 ml) was added, followed by extraction twice with ethyl acetate (50 ml). Chromatography on silica gel with dichloromethane, methanol and conc. ammonia (89:10:1) gave the free base of title compound yield 2.2 g, 78%. The corresponding salt was obtained by addition of a diethyl ether and methanol mixture (9:1) saturated with fumaric acid. Mp 142–146° C.

2a:(±)-8-Methyl-3-(3-pyridyl)-8-azabicyclo[3.2.1] oct-2-ene Fumaric Acid Salt Prepared from 8-methyl-8-azabicyclo[3.2.1]octan-3-one according to method a.
Mp 124–126° C.

3a:(±)-8-Methyl-3-(3-quinolinyl)-8-azabicyclo [3.2.1]oct-2-ene Fumaric Acid Salt Prepared from 8-methyl-8-azabicyclo[3.2.1]octan-3-one according to method a. Mp 140.8–143.8° C.

4a:(±)-3-(3-Benzofuryl)-8-methyl-8-azabicyclo [3.2.1]oct-2-ene Fumaric Acid Salt Prepared according to method a. Mp 140.9–142.8° C.

5a:(±)-3-(3-Benzothienyl)-8-methyl-8-azabicyclo [3.2.1]oct-2-ene Fumaric Acid Salt Prepared according to method a. Mp 146.6–149.5° C.

6a:(±)-3-(2-Thiazolyl)-8-Methyl-8-azabicyclo[3.2.1] oct-2-ene Fumaric Acid Salt Prepared from 8-methyl-8-azabicyclo[3.2.1]octan-3-one according to method a
Mp 196.3–198.5° C.

7a:(±)-8-Methyl-3-(2-methoxyphenyl)-8-azabicyclo [3.2.1]oct-2-ene Fumaric Acid Salt Prepared from 8-methyl-8-azabicyclo[3.2.1]octan-3-one according to method a.

8a:(±)-8-Methyl-3-(3-thienyl)-8-azabicyclo[3.2.1] oct-2-ene Hydrochloric Acid Salt Prepared from 8-methyl-8-azabicyclo[3.2.1]octan-3-one according to method a
Mp 117–118.5° C.

9a:(±)-8-Methyl-3-(2-naphtyl)-8-azabicyclo[3.2.1] oct-2-ene Hydrochloric Acid Salt Prepared from 8-methyl-8-azabicyclo[3.2.1]octan-3-one according to method a; Mp 259–264° C.

10a:Exo-8-Methyl-3-(3-pyridyl)-8-azabi cyclo [3.2.1]octane Dihydrochloride

A mixture of endo and exo3-hydroxy-8-Methyl-3-(3-pyridyl)-8-azabicyclo[3.2.1]octane (method a) (1.5 g, 6.9 mmol), Raney nickel (20.0 g, 50% slurry in water) and 50 ml ethanol was stirred under reflux for 15 h. The crude mixture was filtered followed by chromatography an silica gel with dichloromethane, methanol and conc. ammonia (89:10:1) gave the product as free base. The product was converted to the title compound by addition of hydrochloride in ethanol. Mp 275–280° C. Yield 0.55 g, 29%.

11a: Endo-3-hydroxy-3-(3-pyridyl)-8-tert-butoxycarbonyl-8-azabicyclo[3.2.1]octane A mixture of endo-8-benzyl-3-hydroxy-3-(3-pyridyl)-8-azabicyclo[3.2.1]octane (3.0 g, 10.2 mmol), palladium on carbon (5%, 0.80 g), concentrated hydrochloric acid (2 ml) and ethanol (75 ml) was stirred under hydrogen for 15 h. The crude mixture was filtered through celite and evaporated to dryness and stirred with triethylamine (4.1 g, 40.0 mmol), di-(tertbutoxycarbonyl)anhydride (1.75 g, 8.0 mmol) and dichloromethane (50 ml) for 3.5 hours. The crude mixture was evaporated followed by chromatography on silica gel with dichloromethane, methanol and conc. ammonia (89:10:1) which gave the title compound. Mp 90–92° C., yield 2.8 g, 90%.

12a:(±)-3-(3-Pyridyl8-tert-butoxycarbonyl-8-azabicyclo[3.2.1]oct-2-ene

A mixture of Endo-3-hydroxy-3-(3-pyridyl)-8-tert-butoxycarbonyl-8-azabicyclo[3.2.1]octane 2.0 g, 6.6 mmol), thionyl chloride (6 ml, 82 mmol) and tetrahydrofuran (100 ml) was stirred at 50° C. for 0.5 h. The mixture was evaporated and combined with potassium hydroxide (3.0 g, 53 mmol), ethanol (20 ml) and water (20 ml) and stirred for 10 min. The ethanol was evaporated and water (50 ml) was added. The mixture was extracted twice with ethyl acetate (50 ml). Chromatography on silica gel with dichloromethane, methanol and conc. ammonia (89:10:1) gave the title compound as an oil. Yield 0.43 g, 23%.

Method B

1b:(±)-8-H-3-(3-Pyridyl8-azabicyclo[3.2.1]oct-2-ene Fumaric Acid Salt (±)-3-(3-Pyridyl)-8-tert-butoxycarbonyl-8-azabicyclo [3.2.1]oct-2-ene (0.40 g, 1.40 mmol stirred in a mixture of trifluoroacetic acid (3.2 g, 28 mmol) and dichloromethane overnight. Aqueous sodium hydroxide (100 ml, 1 M) was added followed by extraction with dichloromethane (100 ml) three times. Chromatography on silica gel with dichloromethane, methanol and conc. ammonia (89:10:1) gave the title compound pure. The corresponding salt was obtained by addition of a diethyl ether and methanol mixture (9:1) saturated with fumaric acid. Yield 0.13 g, 31%. Mp 175–176° C.

2b:(±)-8-Methyl-3-trifluoramethanesulfonyl-oxy-8-azabicyclo[3.2.1]oct-2-ene

To 8-methyl-8-azabicyclo[3.2.1]octan-3-one (12.65 g, 90.9 mmol) in tetrahydrofuran (300 ml), was added at −70°

C.; sodium bis(trimethylsilyl)amide in tetrahydrofuran (77.5 ml, 77.5 mmol).

The reaction mixture was stirred for 30 min at −70° C. N-phenylbis(trifluoromethane-sulfonamide) (32.5 g, 90.9 mmol) in tetrahydrofuran (200 ml) was added at −70° C. The reaction mixture was allowed to reach room temperature slowly and was stirred over night. Aqueous sodium hydroxide (0.1 M, 500 ml) was added and the mixture was extracted twice with ethyl acetate (200 ml). Chromatography on silica gel with dichloromethane and 10% ethanol as solvent gave the title compound as an oil. Yield 16.2 g, 45%.

3b:(±)-8-Methyl-3-[3-(6-methoxy)pyridyl]-8-azabicyclo[3.2.1]oct-2-ene

A mixture of (±)-8-Methyl-3-trifluoromethanesulfonyloxy-8-azabicyclo[3.2.1]oct-2-ene (3.0 g 12.2 mmol), hexamethyiditin (4.0 g, 12.2 mmol), bis(triphenylphosphine)palladium(II)-dichloride (0.43 g, 0.61 mmol) and lithium chloride (0.52 g, 12.3 mmol) was stirred in 1.4-dioxane (25 ml) at 70° C. for 2 h. Then 3-Bromo-6-methoxypyridine (4.6 g, 24.4 mmol) was added followed by stirring at reflux overnight. The solvent was evaporated and aqueous sodium hydroxide (30 ml, 1 M) was added followed by extraction three times with ethyl acetate is (30 ml). Chromatography on silica gel with dichloromethane, methanol and conc. ammonia (89:10:1) gave the title compound as an oil. Yield 1.0 g, 36%.

4b:(±)-3-Acetyl-8-methyl-8-azabicyclo[3.2.1]oct-2-ene Fumaric Acid Salt

A mixture of (±)-8-Methyl-3-trifluoromethanesulfonyloxy-8-azabicyclo[3.2.1]oct-2-ene (2.0 g, 7.4 mmol), 1-methoxy-1-trimethylstannylethylene (2.45 g, 11.1 mmol), bis(triphenylphosphine)palladium(II)-dichloride (0.26 g, 0.37 mmol) and lithium chloride (0.31 g, 7.4 mmol) was stirred in tetrahydrofuran (30 ml) at reflux overnight. The solvent was evaporated. Sodium hydroxide (40 ml, 1 M) was added and the mixture was extracted with ethyl acetate. Mp 148.5–150° C. Chromatography on silica gel with dichloromethane, methanol and conc. ammonia (89:10:1) gave (±)-3-(1-methoxy-1-ethenyl)-8-methyl-8-azabicyclo[3.2.1]oct-2-ene fumaric acid salt (0.23 g, 17%) which was mixed with hydrogen chloride in methanol (10 ml, 4.5 M) and stirred for 10 min. The mixture was evaporated to dryness and sodium ethoxide (0.19 g, 8.4 mmol) was added. Chromatography of this crude mixture on silica gel with dichloromethane, methanol and conc. ammonia (89:10:1) gave the title compound. The corresponding salt was obtained by addition of a diethyl ether and methanol mixture (9:1) saturated with fumaric acid. Yield 0.21 g, 58%. Mp 175–176° C.

5b:(±)-8-Methyl-3-[3-(6-chloro)pyridyl]-8-azabicyclo[3.2.1]oct-2-ene Fumaric Acid Salt A mixture of (±)-8-Methyl-3-3-(6-methoxy)pyridyl]-8-azabicyclo[3.2.1]oct-2-ene (0.50 g, 2.13 mmol) and phosphorus oxychloride (4 ml) in dimethylformamide (5 ml) was stirred overnight at 95° C. Ice (100 g) and aqeous sodium hydroxide (4 M, 50 ml) was added followed by extraction three times with ethyl acetate (50 ml). Chromatography on silica gel with dichloromethane, methanol and conc. ammonia (89:10:1) gave the title compound as an oil. The corresponding salt was obtained by addition of a diethyl ether and methanol mixture (9:1), saturated with fumaric acid. Yield 0.35 g, 47%. Mp 140–142° C.

6b:(±)-8-Methyl-3-trifluoromethanesulfonyl-oxy-8-azabicyclo[3.2.1]oct-2-ene

To 8-methyl-8-azabicyclo[3.2.1]octan-3-one (9.35 g, 67.2 mmol) in tetrahydrofuran, was added at −70° C.: sodium bis(trimethylsilyl)amide in tetrahydrofuran (73.9 ml, 73.9 mmol). The reaction mixture was stirred for 10 min. N-phenylbis(trifluoromethanesulfonamide) (24.0 g, 67.2 mmol) in tetrahydrofuran was added at −70° C. The reaction mixture was allowed to reach room temperature slowly and was stirred over night. Aqueous sodium hydroxide (0.1 M, 350 ml) was added and the mixture was extracted twice with 150 ml ethyl acetate. Chromatography on silica gel with dichloromethane and 10% ethanol as solvent gave the title compound as a brown oil. Yield 11.6 g, 70%.

Method C

1c:(±)-3-(2-Benzofuryl)-8-methyl-8-azabicyclo[3.2.1]oct-2-ene Fumaric Acid Salt

A mixture of (±)-8-Methyl-3-trifluoromethanesulfonyloxy-B-azabicyclo[3.2.1]oct-2-ene (1.5 g 6.1 mmol), benzofuran-2-boronic acid (0.99 g, 6.1 mmol), tetrakis(triphenyl-phosphine)-palladium(0) (0.07 g, 0.06 mmol) and lithium chloride (0.26 g, 6.1 mmol), potassium carbonate (4.2 g, 30.5 mmol), water (15 ml) and 1,2-dimethoxyethane (15 ml) was refluxed for 1.5 h. Water (50 ml) was added and the mixture was extracted twice with ethyl acetate (50 ml). Chromatography on silica gel with dichloromethane, methanol and conc. ammonia (89:10:1) gave the title compound. The corresponding salt was obtained by addition of a diethyl ether and methanol mixture (9:1), saturated with fumaric acid. Yield 0.24 g, 11%. Mp 188.3–190.9° C.

2c:(±)-3-(2-Benzothienyl)-8-methyl-8-azabicyclo[3.2.1]oct-2ene

Prepared according to method c. Mp 81.0–83.6° C.

3c:(±)-3-(3-Acetamidophenyl)-8-methyl-8-azabicyclo[3.2.1]oct-2-ene Fumaric Acid Salt Prepared according to method c from 3-acetamidobenzeneboronic acid. Mp 195.3–196.9° C.

4c:(±)-3-(3-Aminophenyl) 8-methyl-8-azabicyclo[3.2.1]oct-2-ene Fumaric Acid Salt A mixture of (±)-3-(3-Acetamidophenyl)-8-methyl-8-azabicyclo[3.2.1]oct-2-ene (0.32 g, 1.25 mmol) and hydrochloric acid (25 ml, 25%) was stirred at reflux overnight. The mixture was evaporated to dryness. Aqueous sodium hydroxide (1 M, 50 ml) was added and the mixture was extracted twice with ethyl acetate (50 ml) Mp 195.3–196.9° C. Yield 0.22 g, 52%.

Method D

1d:(±)-3-(2-Benzofuryl)-8-methyl-8-azabicyclo[3.2.1]oct-2-ene Fumaric Acid Salt

To a mixture of benzofuran (20.0 g, 169.3 mmol) and diethyl ether (200 ml), butyllithium in hexanes (2.5 M, 75 ml, 186 mmol) was added at 0° C. The mixture was stirred at 0° C. for 0.5 h and then cooled to −70° C. 8-benzyl-8-azabicyclo[3.2.1]octan-3-one (23.0 g, 169.3 m solved in diethyl ether (150 ml) was added at −70° C. and stirred for 1 h. The reaction mixture was allowed to warm to room temperature ovemight. Water (200 ml) was added and endo and exo-3-(2-benzofuryl)-3-hydroxy-8-methyl-8-azabicyclo[3.2.1]octane was isolated by filtration. Yield 38.7 g, 89%. A mixture of endo and exo-3-(2-benzofuryl)-3-hydroxy-8-methyl-8-azabicyclo[3.2.1]octane (30.0 g, 116.6 mmol), conc. hydrochloric acid (35 ml) and ethanol (300 ml) was stirred at reflux for 1 h. The solvent was evaporated. Sodium hydroxide (150 ml, 4M) was added and the mixture was extracted twice with ethyl acetate (100 ml). (±)-3-(2-benzofuranyl)-8-methyl-8-azabicyclo[3.2.1]oct-2-ene was isolated, yield 18.9 g, 70%. The corresponding salt was obtained by addition of a diethyl ether and methanol mixture (9:1), saturated with fumaric acid. Mp 188.5–191.2° C.

2d:(±)-3-(2-Benzothienyl)-8-methyl-8-azabicyclo [3.2.1]oct-2-ene Hydrochloride

Prepared according to method d. Mp>250° C.

3d:(±)-3-(2-Thienyl)-8-methyl-8-azabicyclo[3.2.1] oct-2-ene Fumaric Acid Salt

Prepared according to method d. Mp 141.5–143.5° C.

4d:(±)-3-[2-(3-Methoxymethylthienyl)]-8-methyl-8-azabicyclo[3.2.1]oct-2-ene

Prepared according to method d. Isolated as an oil.

5d:(±)-3-(2-Benzothiazolyl)-8-methyl-8-azabicyclo [3.2.1]oct-2-ene Fumaric Acid Salt Prepared according to method d. Mp 195–196.8° C.

6d:(±)-3-[2-(1-Methylindolyl)]-8-methyl-8-azabicyclo[3.2.1]oct-2-ene Fumaric Acid Salt Prepared according to method d, with exception of the metalation temperature, at reflux and 1.2 eqv. of tetramethylethylenediamine.

7d:(±)-3-(2-Furyl)-8-methyl-8azabicyclo[3.2.1]oct-2-ene

Prepared according to method d. Isolated as an oil.

8d:(±)-3-(2-Thieno[3.2-b]thienyl)-8-methyl-8-azabicyclo[3.2.1]oct-2-ene Oxalic Acid Salt Prepared according to method d. Mp 48–50° C.

9d:(±)-3-(2-Thieno[2.3-b]thienyl)-8-methyl-8-azabicyclo[3.2.1]oct-2-ene Oxalic Acid Salt Prepared according to method d. Mp 46–48° C.

10d:(±)-3-(2-selenophenyl)8-methyl-8-azabicyclo [3.2.1]oct-2-ene

Prepared according to method d. Mp 176.8–178.3° C.

Method E

1e:(±)-3-(2-Benzofuryl)-8-H-8-azabicyclo[3.2.1]oct-2-ene Fumaric Acid Salt

A mixture of (±)-3-(2-Benzofuryl)-8-methyl-8-azabicyclo [3.2.1]oct-2-ene (5.4 g, 22.6 mmol), 1-chloroethylchloroformate (5.0 g, 34.7 mmol) and xylen (25 ml) was stirred at reflux overnight. Methanol was added and the mixture was stirred 2h at reflux. Sodium hydroxide (4 M, 50 ml) was added at room temperature and the mixture was extracted with ethyl acetate. Chromatography on silica gel with dichloromethane, methanol and conc. ammonia (89:10:1) gave the title compound. The corresponding salt was obtained by addition of a diethyl ether and methanol mixture (9:1) saturated with fumaric acid. Yield 2.58 g, 33%. Mp 201–204° C.

2e:(±)-3-[3-(3-Furyl)-2-thienyl]-8-H-8-azabicyclo [3.2.1]oct-2-ene Fumaric Acid Salt Prepared from (±)-3-[3-(3-furyl)-2-thienyl]-8-methyl-8-azabicyclo[3.2.1]oct-2-ene according to method E. Mp 187–189° C.

3e:(±)-3-(2-Benzofuryl)-8ethyl-8-azabicyclo[3.2.1] oct-2-ene Fumaric Acid Salt

A mixture of (±)-3-(2-Benzofuryl)-8-H-8-azabicyclo [3.2.1]oct-2-ene (1.5 g, 6.7 mmol), bromoethane (0.80 g, 7.3 mmol), diisopropylethylamine (0.87 g, 6.7 mmol) and DMF (50 ml) was stirred for 2h. Sodium hydroxide (100 ml, 1 M) was added followed by extraction twice with diethylether (100 ml). Chromatography on silica gel with dichloromethane, methanol and conc. ammonia (89:10:1) gave the title compound. The corresponding salt was obtained by addition of a diethyl ether and methanol mixture (9:1), saturated with fumaric acid. Yield 0.77 g, 31%. Mp 197–203° C.

Method F

1f:(±)-3-[2-(3-bromothienyl)]-8-methyl-8-azabicyclo [3.2.1]oct-2-ene Fumaric Acid Salt To a solution of 3-bromothiophene (25.0,153.3 mmol) in THF (250 ml) was added: lithiumdiisopropylamide (2 M, 168.7 mmol) at −80° C. The mixture was stirred for 1 h at −80° C. followed by addition of tropinone (21.3 g, 153.3 mmol) in THF (200 ml). The mixture was stirred at −80° C. for 1 h and was allowed to reach roomtemperature overnight. Sodium hydroxide (1 M, 200 ml) was added and extracted three times with diethylether (300 ml). Chromatography on silica gel with dichloromethane, methanol and conc. ammonia (89:10:1) gave endo and exo-3-[3-bromo-(2-thienyl)]-3-hydroxy-8-methyl-8-azabicyclo[3.2.1] octane.

Yield 8.90 g, 19%.

A mixture of endo and exo-3-[3-bromo-(2-thienyl)]-3-hydroxy-8-methyl-8-azabicyclo[3.2.1]octane (8.85 g, 29.3 mmol) and concentrated hydrochloric acid was stirred for 2 h. The hydrochloric acid was evaporated and sodium hydroxide (1 M, 200 ml) was added and the mixture was extracted twice with ethyl acetate (100 ml). Yield 8.3 g, 100%. The corresponding salt was obtained by addition of a diethyl ether and methanol mixture (9:1), saturated with fumaric acid. Mp 130–132° C.

2f:(±)-3-[2-(3-Bromobenzofuryl)]-8-methyl-8-azabicyclo[3.2.1]oct-2-ene Fumaric Acid Salt Prepared according to method F. Mp 161.4–163.3° C.

3f:(±)-3-[2-(3-Bromobenzothienyl)]-8-methyl-8-azabicyclo[3.2.1]oct-2-ene Fumaric Acid Salt Prepared according to method F. Mp 165.0–166.9° C.

4f:(±)-3-[2-(3-Chlorothienyl)]8-methyl-B-azabicyclo [3.2.1]oct-2-ene Fumaric Acid Salt Prepared according to method F. Mp 151.5–153.5° C.

5f:(±)-3-[3-(3-Furyl)-2-thienyl]-8-methyl-8azabicyclo[3.2.1]oct-2-ene Fumaric Acid Salt A mixture of (±)-3-[2-(3-bromothienyl)]-8-ethyl-8-azabicyclo[3.2.1]oct-2-ene (2.0 g, 7.0 mmol), 3-furylboronic acid (0.94 g, 8.4 mmol), tetrakis (triphenylphosphine)-palladium(0) (0.16 g, 0.14 mmol), aqueous potassium carbonate (10.5 ml, 2 M), 1,3-propanediol (2.66 g, 35 mm ol), 1,2-dimethoxyethane (30 ml) and dioxane (50 ml) was stirred at reflux overnight. Sodium hydroxide (50 ml) was added and the mixture was extracted twice with ethyl acetate (50 ml). Chromatography on silica gel with dichloromethane, methanol and conc. ammonia (89:10:1) gave the title compound. The corresponding salt was obtained by addition of a diethyl ether and methanol mixture (9:1) saturated with fumaric acid. Yield 1.59 g, 59%. Mp 187–189° C.

What is claimed is:

1. An 8-azabicyclo[3.2.1]oct-2-ene compound of Formula 1,

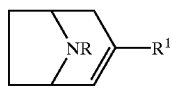

any of its enantiomers or any mixture of its enantiomers, or a pharmaceutically acceptable salt thereof;

wherein R is hydrogen, $C_{1-6}$-alkyl, phenyl, or benzyl; and

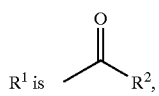

$R^1$ is wherein $R^2$ is hydrogen or $C_{1-6}$-alkyl; or furanyl, thienyl, oxazolyl, isoxazolyl, pyridyl, or thiazolyl, which heteroaryl group is optionally substituted one or more times with substituents selected from the group consisting of $C_{1-6}$-alkyl, $C_{1-6}$-alkoxy, halogen, $CF_3$, $OCF_3$, CN, nitro and furyl.

2. The 8-azabicyclo[3.2.1]oct-2-ene compound of claim 1, wherein

R is hydrogen, methyl, ethyl or benzyl; and $R^1$ is acetyl, 3-pyridyl, 3-(6-methoxy)pyridyl, 3-(6-chloro)pyridyl, 2-thiazolyl, 3-thienyl, 2-thienyl, 2-(3-methoxymethyl)thienyl, 2-furyl, 3-furyl, 2-(3-bromo) thienyl), 3-chloro-thien-2-yl or 3-(3-furyl)-2-thienyl.

3. The 8-azabicyclo[3.2.1]oct-2-ene compound of claim 1, which is (±)-8-Methyl-3-(3-pyridyl)-8-azabicyclo[3.2.1]oct-2-ene;
(±)-3-(2-Thiazolyl)-8-Methyl-8-azabicyclo[3.2.1]oct-2-ene;
(±)-8-Methyl-3-(3-thienyl)-8-azabicyclo[3.2.1]oct-2-ene;
Exo-8-Methyl-3-(3-pyridyl)-8-azabicyclo[3.2.1]octane;
(±)-8-H-3-(3-Pyridyl)-8-azabicyclo[3.2.1]oct-2-ene;
(±)-8-Methyl-3-[3-(6-methoxy)-pyridyl)]-8-azabicyclo[3.2.1]oct-2-ene;
(±)-3-Acetyl-8-methyl-8-azabicyclo[3.2.1]oct-2-ene;
(±)-8-Methyl-3-[3-(6-chloro)-pyridyl]-8-azabicyclo[3.2.1]oct-2-ene;
(±)-3-(2-Thienyl)-8-methyl-8-azabicyclo[3.2.1]oct-2-ene;
(±)-3-(2-Furyl)-8-methyl-8-azabicyclo[3.2.1]oct-2-ene;
(±)-3-[3-(3-Furyl)-2-thienyl]-8-H-8-azabicyclo[3.2.1]oct-2-ene;
(±)-3-[2-(3-Bromothienyl)]-8-methyl-8-azabicyclo[3.2.1]oct-2-ene;
(±)-3-[2-(3-Bromobenzothienyl)]-8-methyl-8-azabicyclo[3.2.1]oct-2-ene;
3-[2-(3-Chlorothienyl)]-8-methyl-8-azabicyclo[3.2.1]oct-2-ene; or
(±)-3-[3-(3-Furyl)-2-thienyl]-8-methyl-8-azabicyclo[3.2.1]oct-2-ene;

or a pharmaceutically acceptable addition salt thereof.

4. A method for the preparation of the 8-azabicyclo[3.2.1] oct-2-ene compound according to claim 1, which method comprises:

a) the step of reacting a compound having the formula

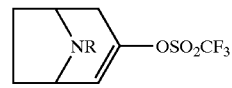

wherein R is as defined above,
with a compound of formula $R^1$—X,
wherein $R^1$ is as defined in claim 1, and X is halogen, boronic acid, or trialkylstannyl; or b) the step of reducing a compound having the formula

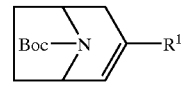

wherein $R^1$ is as defined in claim 1.

5. A method of treating a human being or animal suffering from chemical substance addiction comprising administering to said human being or animal in need thereof a therapeutically effective amount of the 8-azabicyclo[3.2.1] oct-2-ene compound of any one of claims 1, 2, or 3.

6. The method according to claim 5, wherein the chemical substance is tobacco.

* * * * *

UNITED STATES PATENT AND TRADEMARK OFFICE
CERTIFICATE OF CORRECTION

PATENT NO. : 6,645,977 B1
APPLICATION NO. : 09/450637
DATED : November 11, 2003
INVENTOR(S) : Dan Peters et al.

It is certified that error appears in the above-identified patent and that said Letters Patent is hereby corrected as shown below:

Col 23   lines 37-48, through Col. 24   lines 1-17 should be
3. The 8-azabicyclo[3.2.1]oct-2-ene compound of claim 2, which is
(±)-8-Methyl-3-(3-pyridyl)-8-azabicyclo[3.2.1]oct-2-ene;
(±)-3-(2-Thiazolyl)-8-Methyl-8-azabicyclo[3.2.1]oct-2-ene;
(±)-8-Methyl-3-(3-thienyl)-8-azabicyclo[3.2.1]oct-2-ene;
Exo-8-Methyl-3-(3-pyridyl)-8-azabicyclo[3.2.1]octane;
(±)-8-H-3-(3-Pyridyl)-8-azabicyclo[3.2.1]oct-2-ene;
(±)-8-Methyl-3-[3-(6-methoxy)-pyridyl)]-8-azabicyclo[3.2.1]oct-2-ene;
(±)-3-Acetyl-8-methyl-8-azabicyclo[3.2.1]oct-2-ene;
(±)-8-Methyl-3-[3-(6-chloro)-pyridyl]-8-azabicyclo[3.2.1]oct-2-ene;
(±)-3-(2-Thienyl)-8-methyl-8-azabicyclo[3.2.1]oct-2-ene;
(±)-3-(2-Furyl)-8-methyl-8-azabicyclo[3.2.1]oct-2-ene;
(±)-3-[3-(3-Furyl)-2-thienyl]-8-H-8-azabicyclo[3.2.1]oct-2-ene;
(±)-3-[2-(3-Bromothienyl)]-8-methyl-8-azabicyclo[3.2.1]oct-2-ene;
~~(±)-3-2[-(3-Bromobenzothienyl)]-8-methyl-8-azabicyclo[3.2.1]oct-2-ene;~~
3-[2-(3-Chlorothienyl)]-8-methyl-8-azabicyclo[3.2.1]oct-2-ene; or
(±)-3-[3-(3-Furyl)-2-thienyl]-8-methyl-8-azabicyclo[3.2.1]oct-2-ene;
or a pharmaceutically acceptable addition salt thereof.

Signed and Sealed this

Fifteenth Day of August, 2006

JON W. DUDAS
*Director of the United States Patent and Trademark Office*